United States Patent [19]

Linkwitz et al.

[11] Patent Number: 5,221,278
[45] Date of Patent: Jun. 22, 1993

[54] OSMOTICALLY DRIVEN DELIVERY DEVICE WITH EXPANDABLE ORIFICE FOR PULSATILE DELIVERY EFFECT

[75] Inventors: Andreas Linkwitz, Cologne, Fed. Rep. of Germany; Judy A. Magruder, Mountain View; Sonya Merrill, Redwood City, both of Calif.

[73] Assignee: ALZA Corporation, Palo Alto, Calif.

[21] Appl. No.: 849,910

[22] Filed: Mar. 12, 1992

[51] Int. Cl.⁵ .............................................. A61K 9/22
[52] U.S. Cl. ............................ 604/890.1; 604/891.1; 604/892.1; 424/457; 424/468
[58] Field of Search ............... 604/890.1, 891.1, 892.1; 424/457, 468

[56] References Cited

U.S. PATENT DOCUMENTS

| | | | |
|---|---|---|---|
| 3,684,136 | 8/1972 | Baumann | 222/386 |
| 3,788,327 | 1/1974 | Donowitz et al. | 128/350 |
| 4,439,196 | 3/1984 | Higuchi | 604/890 |
| 4,566,493 | 1/1986 | Edwards et al. | 137/846 |
| 4,701,166 | 10/1987 | Groshong et al. | 604/247 |
| 4,723,958 | 2/1988 | Pope et al. | 604/890.1 |
| 4,753,640 | 6/1988 | Nichols et al. | 604/247 |
| 4,777,049 | 10/1988 | Magruder et al. | 424/457 |
| 4,842,867 | 6/1989 | Ayer et al. | 424/473 |
| 4,874,388 | 10/1989 | Wong et al. | 604/891.1 |
| 4,895,346 | 1/1990 | Steigerwald | 604/149.1 |
| 4,957,494 | 9/1990 | Wong et al. | 604/892.1 |
| 5,023,088 | 6/1991 | Wong et al. | 424/473 |
| 5,030,216 | 7/1991 | Theeuwes et al. | 604/892.1 |

Primary Examiner—Randall L. Green
Assistant Examiner—R. Clarke
Attorney, Agent, or Firm—Jacqueline S. Larson; Paul L. Sabatine; Steven F. Stone

[57] ABSTRACT

A drug delivery capsule from which the delivery of the drug is driven by the osmotic infusion of moisture by the capsule from a physiological environment is provided with a delivery orifice which opens intermittently to achieve a pulsatile delivery effect. The wall in which the orifice is formed is constructed of an elastic material, preferably an elastomer, which stretches under a pressure differential caused by the pressure rise inside the capsule as the osmotic infusion progresses. The orifice is small enough that when the elastic wall is relaxed, the flow rate of drug through the orifice is substantially zero, but that when the elastic wall is stretched due to the pressure differential across the wall exceeding a threshold, the orifice expands sufficiently to allow the release of the drug at a physiologically beneficial rate.

9 Claims, 8 Drawing Sheets

OSMOTICALLY DRIVEN DELIVERY DEVICE WITH EXPANDABLE ORIFICE FOR PULSATILE DELIVERY EFFECT

This invention lies in the field of controlled- or sustained-release systems for the delivery of drugs, nutrients and the like. In particular, this invention relates to osmotic delivery systems, which are generally in the form of capsules designed to release a beneficial agent through an orifice in the capsule, the release occurring gradually as the result of internal pressure resulting from the imbibition of fluid by the capsule from a surrounding medium.

BACKGROUND OF THE INVENTION

Osmotic delivery capsules, commonly referred to as "osmotic pumps," function by virtue of walls which selectively pass water into the capsule reservoir. Absorption of water by the capsule through these walls is driven by a water-attracting agent in the capsule interior which creates osmotic pressure across the capsule wall. The water-attracting agent may be the beneficial agent itself whose controlled release is sought, but in most cases, it is a separate agent specifically selected for its ability to draw water, this separate agent being isolated from the beneficial agent at one end of the capsule. In either case, the structure of the capsule wall does not permit the capsule to expand, and as a result, the water uptake causes discharge of the beneficial agent through an orifice in the capsule at the same rate that water enters by osmosis.

The terms "osmotically effective" and "osmotically active" are used in the literature to characterize the water-attracting agent which drives the osmotic flow. Certain agents of this type are termed "osmagents," which denotes water-soluble compounds to which the capsule wall is not permeable. Osmotically effective agents which are polymeric species are termed "osmopolymers," which term denotes water-swellable polymers. Osmagents and osmopolymers may be used individually in a capsule or they may be present as a mixture of the two. In cases where the osmotically active agent is separated from the beneficial agent by a movable partition or piston, the osmotically active agent and the compartment in which it resides may be referred to as an "osmotic engine."

Many protocols or situations require, or would benefit from, an intermittent or pulsatile release of the beneficial agent from the capsule. This is true of a variety of drugs, medicaments and nutriments, in a range of environments extending from veterinary medicine to human drug administrations, and to hobby situations such as fish tanks. The reasons vary, and may address such needs as mimicking a natural intermittent physiological release, allowing for periods of restoration of certain bodily functions between administrations, or adhering to preestablished feeding protocols. A pulsed release may increase the therapeutic index of some drugs which would allow for a lower total dose in those cases. On the hobby level, pulsed release may be used to feed fish while one is away on vacation. Other examples abound.

Among the patent literature on pulsatile osmotic pumps is U.S. Pat. No. 4,777,049, issued Oct. 11, 1988 to Magruder, P. R., et al. The pulsatile effect in this patent is achieved by combining the beneficial agent with a modulating agent. The modulating agent is selected on the basis of its solubility in the delivery medium relative to the beneficial agent, and the pulsatile effect results from one of the two agents falling below its saturation point, causing more of the other to go into solution and to thereby be released. The number of pulses one may obtain in this manner is limited, however, and it is difficult to achieve periodic pulses. The system of U.S. Pat. No. 4,723,958, issued Feb. 9, 1989 to Pope, D. G., et al. achieves the pulsatile effect by alternating layers of beneficial agent with layers of inert material. During its release, however, the beneficial agent emerges at a slow rate. The system of U.S. Pat. No. 4,842,867, issued Jun. 27, 1989 to Ayer, A. D., et al., is also a layered system, and is most effective with a low number of pulses. Layered systems are also disclosed by Wong, P. S. L., et al., U.S. Pat. No. 4,874,388, issued Oct. 17, 1989; Wong, P. S. L., et al., U.S. Pat. No. 4,957,494, issued Sep. 18, 1990; and Wong, P. S. L., et al., U.S. Pat. No. 5,023,088, issued Jun. 11, 1991.

SUMMARY OF THE INVENTION

The present invention resides in an osmotic delivery capsule which produces an intermittent or pulsatile release of the beneficial agent by virtue of the structure of the capsule itself rather than the chemical composition or placement of materials contained in the capsule. The intermittent or pulsatile release is produced by forming the orifice in a wall section of elastic material that stretches in response to the osmotic pressure, the orifice being small enough to remain closed, or at least substantially closed, when the osmotic pressure is below a threshold level, and yet opening as the elastic material stretches when the osmotic pressure exceeds the threshold. As the capsule absorbs moisture continuously in an aqueous environment, the absorbed moisture causes the pressure inside the capsule to rise until the threshold is reached, at which time the orifice opens to release beneficial agent until the pressure is sufficiently relieved to cause the orifice to reclose. The cycle is repeated until the beneficial agent is depleted or the capsule is removed from the aqueous environment.

In preferred embodiments of the invention, certain additional features are included which enhance the performance of the device. Prominent among these features is a movable partition which divides the capsule interior into two compartments, one for the beneficial agent and the other for a water-attracting agent (the "osmotic engine") distinct from the beneficial agent. The orifice in these embodiments is located in a portion of the capsule wall surrounding the beneficial agent compartment, preferably at a location which remains on the beneficial agent side of the partition at all times during the travel of the partition. In embodiments where the capsule is an elongated structure, the partition moves longitudinally, and the orifice is preferably in an end wall.

The pressure build-up in the osmotic engine compartment due to the inward diffusion of water is transmitted through the partition to the beneficial agent compartment while the partition prevents the contents of the two compartments from mixing. When the pressure in the beneficial agent compartment exceeds the threshold and causes the orifice to open, an amount of beneficial agent sufficient to relieve the pressure in the beneficial agent compartment is expelled through the orifice. This release of pressure causes the elastic material to relax and thereby close the orifice. The movement of the partition inside the capsule is essentially unrestricted, the capsule walls offering substantially no resistance to the movement of the partition along the longitudinal axis of the capsule. The partition may therefore be a simple solid plug or disk of fluid-impermeable construction.

In further preferred embodiments, the elastic material surrounding the orifice forms the entire end wall of the capsule, permitting maximum distortion of the material and thus a maximum opening of the orifice in response to the pressure differential. In still further preferred embodiments, the elastic material is not moisture-permeable, nor is any of the wall material surrounding the beneficial agent compartment over the entire range of motion of the partition. The moisture-permeable wall in these embodiments does not extend beyond the osmotic engine compartment, and moisture diffusion into the capsule will thus occur only in the osmotic engine compartment.

Further preferred embodiments and their features, and further objects and advantages of the invention, will be apparent from the description which follows.

DETAILED DESCRIPTION OF THE INVENTION AND PREFERRED EMBODIMENTS

Figure 1:
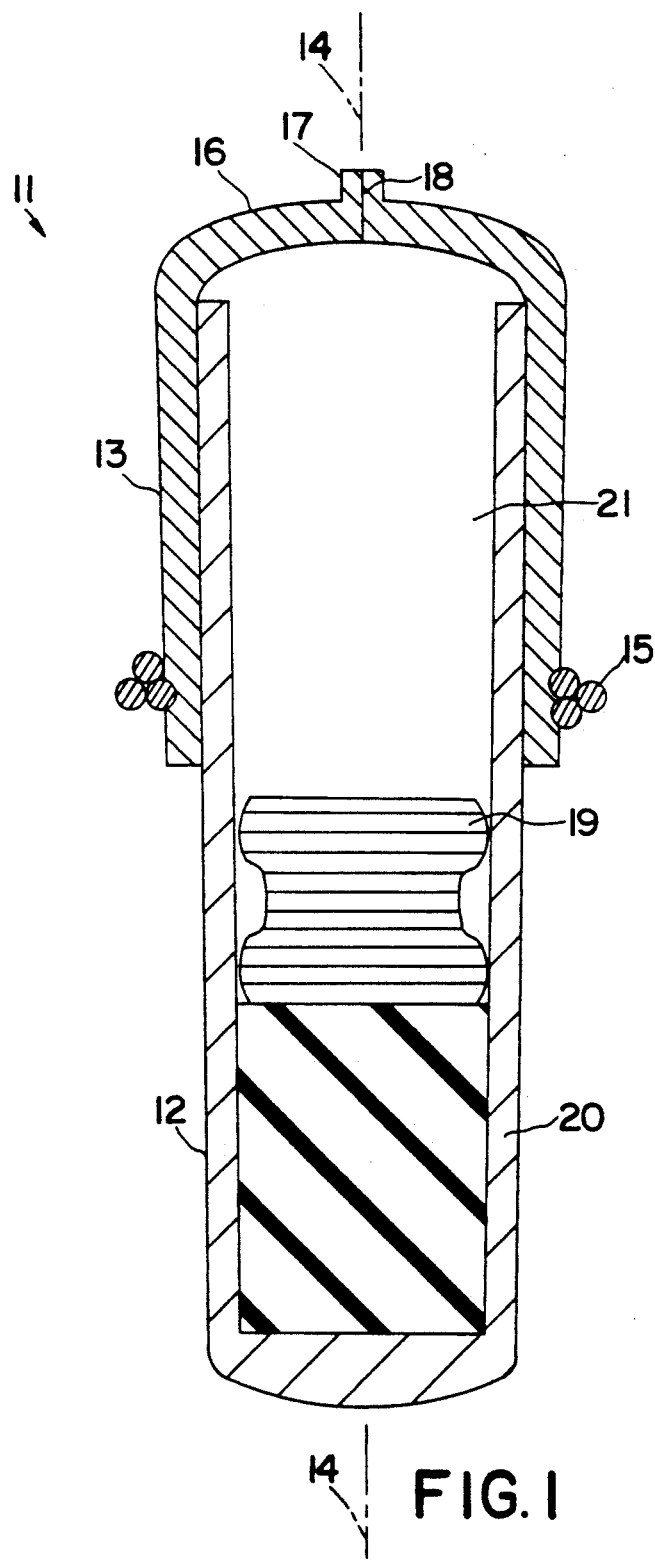
FIG. 1 is a side cross-section view of one example of an osmotic delivery device in accordance with this invention for pulsatile delivery.

The pulsatile effect achieved by a device constructed in accordance with this invention, including the length of time between pulses and the sharpness of the pulse, can be controlled by one or more of several parameters. These include the selection of the materials from which the device is constructed, the configuration of the device and its dimensions, and other variables. The degree and manner in which the pulsatile effect can be controlled by these parameters is predictable in some cases, ascertainable by calculation in others, and in still others ascertainable by routine experimentation. These parameters include, for example, the choice of elastic material, the thickness of the wall section made from the elastic material, the lateral dimensions of the elastic wall section, the configuration and location of the orifice, and the viscosity and surface tension of the beneficial agent formulation. Additional parameters indirectly affecting the pulsatile effect include the osmotic engine, notably the moisture permeability of the wall surrounding the osmotic engine and the absorptive properties of the osmotic engine itself. With appropriate selection and control of these parameters, the interval between pulses may range from minutes to days, and is preferably within the range of from about six hours to about two days.

The elastic material itself may be any material which stretches under a pressure differential and then returns to its original configuration once the pressure differential is removed, and in which a hole can be formed which will remain substantially closed when the material is relaxed and yet open when the material is stretched, resuming its closed configuration when the stretching force is removed. Preferred elastic materials are elastomers, which in general are synthetic high polymers having properties similar to those of vulcanized rubber, namely the ability to stretch to at least twice their original length and to retract very rapidly to approximately their original length when released. Examples are styrene-butadiene copolymer, polychloroprene (neoprene), nitrile rubbers (such as acrylonitrile-butadiene rubber), butyl rubber, polyacrylates, polysulfide rubber (Thiokol), polyisoprenes (such as cis-1,4-polyisoprene), ethylene-propylene terpolymers (such as EPDM), polyepichlorohydrin, polyfluorinated hydrocarbons, silicone rubber and polyurethane rubber. Both cross-linked and uncross-linked polymers may be used, although cross-linked polymers are preferred.

The thickness of the elastic material may vary considerably. Best results are generally obtained with thicknesses of at least about 0.03 cm, preferably at least about 0.06 cm. For those devices which are elongated capsules, the location of the orifice in preferred embodiments of the invention is in the end wall of the device, and the elastic material will surround the orifice. In further preferred embodiments, the elastic material forms the entire end wall of the device so that the end wall in its entirety responds to the stretching force and thereby contributes to the opening and closing of the orifice. The elastic material may also extend back along the sides of the device, although with less effect on the action of the orifice.

The orifice may be constructed to have a channel with a length greater than the thickness of the elastic material forming the end wall of the device, by including a protrusion on the wall and forming the orifice through the protrusion. A longer orifice will generally require a greater pressure differential to open, and once it has opened, will close more securely.

The orifice will be small enough to permit at most a small flow rate of beneficial agent out of the device when relaxed, relative to the flow rate occurring when the surrounding elastic wall material is stretched under stress from internal pressure. Thus, the orifice may close entirely, permitting no outward flow at all, when the pressure differential is below a threshold value, or it may close sufficiently to permit a flow rate which is only a fraction of the flow rate when open. While it is possible to measure the threshold pressure differential, it is not necessary to do so, since the pulsing effect can be detected and characterized by measurements of the amount and rate of beneficial agent released.

The orifice may be formed by any conventional means. One particularly convenient method is by puncturing the elastic wall with a piercing tool, either solid or hollow. A hypodermic syringe, for example, may be used effectively, and the response of the resulting orifice to pressure differentials may be controlled by appropriate selection of the gauge of the syringe needle. The optimal diameter of the piercing member for any particular orifice will vary, depending on the thickness and elasticity of the wall, and on the length of the channel being formed. In most cases, a piercing member having an outer diameter of not more than about 0.015 cm, preferably not more than about 0.010 cm, will provide the best results.

While this invention is of broad scope and capable of implementation in osmotic delivery devices of many different structures and arrangements, as well as with many different types of drugs and other beneficial agents, the basic elements of the invention and their functions are most easily understood by examination of a specific example.

FIG. 1 depicts, in cross section, a capsule in accordance with the invention which provides a pulsatile effect by virtue of an orifice which opens in response to a buildup of pressure inside the capsule. The capsule 11 is constructed from a membrane cup 12 of semi-permeable membrane material, and a cap 13 of elastomeric material. Both are cylindrical in shape, bodies of revolution about a longitudinal axis 14. The cap 13 is secured to the membrane cup 12 by a length of wire 15 wrapped (in this case, three times) around the cap at a location where the cap overlaps the membrane cup.

The cap 13 terminates in an end wall 16 which has a protrusion 17 extending outward at its center. The protrusion is perforated with an orifice 18 which, as described above, opens and closes in response to changes in the pressure differential across the cap wall. The interior of the capsule is divided into two compartments by a partition or piston 19, the two compartments being the osmotic engine compartment 20 and the drug compartment 21. The osmotic engine compartment 20 is occupied by the osmagent and/or osmopolymer, and the drug compartment 21 is occupied by the beneficial agent whose controlled delivery from the capsule is sought.

The capsule 11 is constructed in two parts as shown (membrane cup 12 and cap 13) for various reasons. Prominent among these are the ability to use separate materials of differing properties—a semi-permeable (moisture-permeable), relatively inelastic membrane material for the membrane cup and a fluid-impermeable and relatively elastic material for the cap—and the ability to place the capsule ingredients inside the capsule before the capsule is sealed closed.

Aside from these qualities of permeability and elasticity, the materials of construction of this capsule and all other capsules in accordance with this invention are not critical and may vary widely. The remaining requirements of these materials are merely that they be inert, capable of maintaining structural integrity and of withstanding the stresses encountered during the placement of the capsule in the environment in which it will be used, and during its operation in absorbing moisture and delivering the beneficial agent.

Preferred moisture-permeable materials for the wall surrounding the osmotic engine are cellulosic materials, such as cellulose esters, cellulose ethers and cellulose ester-ethers. Those having a degree of substitution ("D.S."), or average number of substitutions per anhydroglucose unit at hydroxyl group positions, ranging from greater than zero up to and including 3.0, are preferred. Examples are cellulose acylate, cellulose diacylate, cellulose triacylate, cellulose acetate, cellulose diacetate, cellulose triacetate, mono-, di-, and tricellulose alkanylates, and mono-, di-, and tricellulose aroylates. Examples expressed in terms of D.S. ranges are cellulose acetate having a D.S. of 1.0 or less and an acetyl content of 21% or less, cellulose acetate having a D.S. of 1.0 to 2.0 and an acetyl content of 21% to 35%, and cellulose acetate having a D.S. of 2.0 to 3.0 and an acetyl content of 35% to 44.8%. Further examples are cellulose propionate with D.S. of 1.8, a propionyl content of 39.2% to 45%, and a hydroxyl content of 2.8% to 5.4%; cellulose acetate butyrate with D.S. of 1.8, and acetyl content of 13% to 15%, and a butyryl content of 34% to 39%; cellulose acetate butyrate with acetyl content of 17% to 53%, a butyryl content of 17% to 53%, and a hydroxyl content of 0.55 to 4.7%; cellulose acetate butyrate with D.S. of 1.8, and acetyl content of 4% and a butyryl content of 51%; cellulose triacylates with D.S. of 2.9 to 3, such as cellulose trivalerate, cellulose trilaurate, cellulose tripalmitate, cellulose trisuccinate, cellulose trioctanoate; cellulose diacylates with D.S. of 2.2 to 2.6, such as cellulose disuccinate, cellulose dipalmitate, cellulose dioctanoate, and cellulose dipentanoate; and coesters of cellulose such as cellulose acetate butyrate and cellulose acetate propionate.

The moisture permeability of the wall surrounding the osmotic engine may be further controlled by the inclusion of modifiers in the wall composition. Modifiers may be selected either to decrease or to increase the moisture permeability. Examples of modifiers which decrease the permeability are polyacrylate, polymethacrylate, polysulfone, polyacrylic ester, polyacrylonitrile, polyacrylamide, polystyrene, polycaprolactam, polyhexamethylene adipamide, polyhexamethylene sebacamide, polyepoxide, and polyformaldehyde. Examples of modifiers which increase the permeability are polyvinyl alcohol; poly(1,4-anhydro-$\beta$-D-mannuronic acid); polyesters derived from the condensation of a polyhydric alcohol and a polyfunctional acid whose functional groups are hydroxyl groups, carboxyl groups and the like; polysaccharides, hydroxyalkylcelluloses having molecular weights of 9,000 to 35,000; and polyalkylene glycol. Depending on its need, the modifier may be present in the wall material in an amount ranging from about 5% to about 50% by weight.

Physical characteristics of the wall such as workability and flexibility, lowering of the second-order phase transition temperature and modification of the elastic modulus, may further be enhanced by the inclusion of a plasticizer. Typical plasticizers extend to both straight-chain and branched-chain plasticizers, cyclic plasticizers, acrylic plasticizers and heterocyclic plasticizers. Examples of classes of suitable plasticizers are phthalate, phosphate, citrate, adipate, tartrate, sebacate, succinate, glycolate, glycerolate, benzoate, myristate and sulfonamide plasticizers, including halogenated species. Particular plasticizers of interest are dialkyl phthalates such as dimethyl phthalate, dipropyl phthalate, di(2-ethylhexyl) phthalate, and diisopropyl phthalate; dicycloalkyl phthalates; diaryl phthalates; alkyl phosphates; trialkyl phosphates such as tributyl phosphate and trioctyl phosphate; aryl phosphates and triaryl phosphates such as triphenyl phosphate and tricresyl phosphate; alkyl and trialkyl citrates such as tributyl citrate and triethyl citrate; citrate esters such as acetyl triethyl citrate; alkyl adipates such as dioctyl adipate, diethyl adipate and di(2-methoxyethyl) adipate; alkyl and dialkyl tartrates such as butyl tartrate and diethyl tartrate; alkyl and dialkyl sebacates such as diethyl sebacate, dipropyl sebacate, and dinonyl sebacate; alkyl and dialkyl succinates such as diethyl succinate and dimethyl succinate; alkyl glycolates; alkyl glycerolates; glycol esters and glycerol esters such as glycerol diacetate, glycerol triacetate, glycerol monolactate diacetate and methyl phytyl ethyl glycolate. Plasticizers when included will generally comprise from about 1% to about 45% by weight of the wall composition.

The partition separating the osmotic engine from the drug reservoir, and the close-fitting porous or perforated sleeve which is included in certain embodiments of the invention as structural support for the semipermeable membrane (although not shown in FIG. 1), may be constructed of any material which is inert and sufficiently rigid to perform its function effectively. Typical materials of construction suitable for these parts include polyolefins, condensation polymers, addition polymers, organo-silicon polymers and inorganic polymers. Specific examples are high density polyethylene, high density polypropylene, polystyrene, polycarbonate, polyamides, chlorinated rubbers, styrene-butadiene rubbers, chloroprene rubbers, silicones, and glass. Several of these materials are elastomers, but will be used with a thickness which does not permit the degree of expansion which the orifice will exhibit under the same pressure differentials. Examples of common materials available in the industry are those bearing the trade name Santoprene ®, products of Monsanto Company, St. Louis, Mo., U.S.A.

Osmotic delivery capsules in accordance with the present invention may be manufactured by a variety of techniques, many of which are described in the literature. In one such technique, the beneficial agent and the osmotically active agent are prepared as solid or semisolid formulations and pressed into pellets or tablets whose dimensions correspond to the internal dimensions of the respective compartments which they will occupy in the capsule interior. Depending on the nature of the materials used, the two agents and other solid ingredients which may be included with them may be processed prior to the formation of the pellets by such procedures as ballmilling, calendering, stirring, rollmilling, fluid bed granulation or solvent wet granulation to achieve a fine particle size and hence fairly uniform mixtures of each. Once the pellets have been formed, they are placed inside a preformed capsule with the partition in between. The capsule may be formed from any of the wall-forming materials disclosed above by the use of a mold, with the materials applied either over the mold or inside the mold, depending on the mold configuration.

In other embodiments of this invention, the beneficial agents are flowable compositions such as liquids, suspension, or slurries, and are poured into the capsule after the osmotically active agent and the partition have been inserted. Still further alternatives may include any of the wide variety of techniques known in the art for forming capsules used in the pharmaceutical industry.

While methods for forming the capsule orifice are discussed above, the orifice may also be formed by conventional techniques described in the literature. Included among these methods are mechanical drilling, laser drilling, molding and chemical techniques using an orifice forming agent, such as erosion, extraction, dissolving, bursting or leaching, depending on the nature of the agent used. The capsule will contain at least one such orifice, and in most configurations, one orifice will suffice and will in fact be preferred.

Species which fall within the category of osmagent, i.e., the non-volatile species which are soluble in water and create the osmotic gradient driving the osmotic inflow of water, vary widely. Examples are magnesium sulfate, magnesium chloride, potassium sulfate, sodium chloride, sodium sulfate, lithium sulfate, sodium phosphate, potassium phosphate, d-mannitol, sorbitol, inositol, urea, magnesium succinate, tartaric acid, raffinose, and various monosaccharides, oligosaccharides and polysaccharides such as sucrose, glucose, lactose, fructose, and dextran, as well as mixtures of any of these various species.

Species which fall within the category of osmopolymer are hydrophilic polymers that swell upon contact with water, and these vary widely as well. Osmopolymers may be of plant or animal origin, or synthetic. Examples are poly(hydroxy-alkyl methacrylates) with molecular weight of 30,000 to 5,000,000, poly(vinylpyrrolidone) with molecular weight of 10,000 to 360,000, anionic and cationic hydrogels, polyelectrolyte complexes, poly(vinyl alcohol) having low acetate residual, optionally crosslinked with glyoxal, formaldehyde or glutaraldehyde and having a degree of polymerization of 200 to 30,000, a mixture of methyl cellulose, crosslinked agar and carboxymethylcellulose, a mixture of hydroxypropyl methylcellulose and sodium carboxymethylcellulose, polymers of N-vinyl lactams, polyoxyethylene-polyoxypropylene gels, polyoxybutylene-polyethylene block copolymer gels, carob gum, polyacrylic gels, polyester gels, polyurea gels, polyether gels, polyamide gels, polyimide gels, polypeptide gels, polyamino acid gels, polycellulosic gels, Carbopol ® acidic carboxy polymers having molecular weights of 250,000 to 4,000,000, Cyanamer ® polyacrylamides, crosslinked indene-maleic anhydride polymers, Good-Rite ® polyacrylic acids having molecular weights of 80,000 to 200,000, Polyox ® polyethylene oxide polymers having molecular weights of 100,000 to 5,000,000, starch graft copolymers, and Aqua-Keeps ® acrylate polymer polysaccharides.

The term "drug" is used in this specification primarily for purposes of convenience. The present invention applies to the administration of beneficial agents in general, which include any physiologically or pharmacologically active substance. Included among the types of agents which meet this description are biocides, sterilization agents, nutrients, vitamins, food supplements, sex sterilants, fertility inhibitors and fertility promoters. Drug agents include drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autocoid systems, the alimentary and excretory systems, the histamine system and the central nervous system. Suitable agents may be selected from, for example, proteins, enzymes, hormones, polynucleotides, nucleoproteins, polysaccharides, glycoproteins, M. lipoproteins, polypeptides, steroids, analgesics, local anesthetics, antibiotic agents, anti-inflammatory corticosteroids, ocular drugs and synthetic analogs of these species.

Examples of drugs which may be delivered by devices according to this invention are prochlorperazine edisylate, ferrous sulfate, aminocaproic acid, mecaxylamine hydrochloride, procainamide hydrochloride, amphetamine sulfate, methamphetamine hydrochloride, benzphetamine hydrochloride, isoproteronol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindone, diphenadione erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17 β-estradiol, ethinyl estradiol, ethinyl estradiol 3-methyl ether, pednisolone, 17 β-hydroxyprogesterone acetate, 19-norprogesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, capropril, madol, quanbenz, hydrochlorothiazide, ranitidine, flurbiprofen, fenbufen, fluprofen, tolmetin, alolofenac, mefenamic, flufenamic, difuninal, nimodipine, nitrendipine, nisoldipine, nicardipine, felodipine, lidoflazine, tiapamil, gallopamil, amlodipine, mioflazine, lisinolpril, enalapril, captopril, ramipril, endlapriat, famotidine, nizatidine, sucralfate, etintidine, tetratolol, minoxidil, chlordiazepoxide, diazepam, amitriptylin, and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin; gonadotropin releasing hormone, bovine somatropin, porcine somatotropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor.

The beneficial agent can be present in this invention in a wide variety of chemical and physical forms, such as solids, liquids and slurries. On the molecular level, the various forms may include uncharged molecules, molecular complexes, and pharmaceutically acceptable acid addition and base addition salts such as hydrochlorides, hydrobromides, sulfate, laurylate, oleate, and salicylate. For acidic compounds, salts of metals, amines or organic cations can be used. Derivatives such as esters, ethers and amides can be used. An active agent can be used alone or mixed with other active agents.

The pulsatile delivery which is provided by devices in accordance with this invention may be for therapeutic purposes, nutritional purposes, preventive purposes, and a wide variety of situations in general. The environments in which the devices may be used include physiological environments within the body of a human or animal, or aqueous environments such as pools, tanks, reservoirs, and the like, serving recreational, industrial, or residential purposes. Animals to whom drugs may be administered using systems of this invention include humans and other mammals and warm-blooded animals in general, avians, reptiles and fishes. Household animals, sport animals, farm animals, laboratory animals and zoo animals are included. The invention is of particular interest for application to humans and household, sport and farm animals, particularly mammals. Prominent examples other than humans are sheep, goats, cattle, horses and pigs. For the administration of beneficial agents to animals, the devices of the present invention may be implanted subcutaneously or interperitoneally wherein aqueous body fluids are available to activate the osmotic engine.

While the presently preferred embodiment of the delivery device of the present invention is an implant, the invention also extends to devices intended for use in the anal-rectal passageway, in the cervical canal, as an artificial gland, in the vagina, and the like. The invention further extends to devices intended for use as a ruminal bolus for delivery of a beneficial agent within the rumen of a ruminant animal. Devices to be used as ruminal boluses will generally include a density element for maintaining the device in the rumen over an extended period of time. Density elements known in the art are suitable for use in this manner.

The following examples are illustrations of the practice of the invention, and are intended neither to define nor to limit the scope of the invention in any manner.

EXAMPLE 1

This example illustrates the pulsatile effect of an osmotic delivery device in accordance with the present invention.

An osmotic delivery device of the configuration shown in FIG. 1 was prepared as follows:

overall length: approximately 1 inch (2.54 cm)

outer diameter: approximately 0.175 inches (0.44 cm) at the orifice end and approximately 0.153 inches (0.39 cm) at the osmotic engine end wall material surrounding the osmotic engine (membrane cup): 85% cellulose acetate butyrate 500-5, 15% tributyl citrate; moisture-permeable; thickness: 0.030 inch (0.076 cm) at end, 0.016 inch (0.041 cm) at side wall surrounding osmotic engine; 0.030 inch (0.076 cm) at side wall lining drug compartment wall material at the orifice end: styrene butadiene rubber; moisture-impermeable; thickness: 0.020 inch (0.051 cm) (total thickness of side wall, 0.050 inch, 0.127 cm)

partition (piston): Santoprene®271-55, length 0.100 inch (0.254 cm), diameter 0.127 inch (0.32 cm), lubricated with silicone medical fluid 1000 cs to facilitate movement inside the capsule orifice extension: length: 0.005 inch (0.0127 cm), for a total orifice length of 0.025 inch (0.064 cm)

orifice formed by piercing with a 25 gauge needle (having outer diameter of 0.005–0.006 inch, 0.013–0.015 cm)

The materials used inside the capsule were as follows:

| osmotic tablets: | |
|---|---|
| composition: | |
| sodium chloride | 55% |
| sodium carbomer | 36% |
| water | 7% |
| povidone | 1% |
| magnesium stearate | 1% |
| length: | 0.151 inch (0.38 cm) average |
| diameter: | 0.122 inch (0.31 cm) average |
| test composition (for placement in drug compartment): blue dye | |

-continued osmotic tablets:

1 in glycerol at concentrations of 41.5 mg/100 mL glycerol and 97.0 mg/100 mL glycerol The test capsules were assembled by first inserting two osmotic tablets in a stack in the membrane cup, then placing the piston on top of the tablet stack. The elastomeric bag for enclosing the drug end of the capsule was then sealed over the membrane cup by crimping with wire. The compartment above the piston was then filled with one of the blue dye/glycerol solutions by syringe with a 25-gauge needle. The amount added was approximately 0.2 cc.

Several capsules thus prepared were placed in test tubes containing distilled water, and the test tubes were placed in a water bath maintained at 37° C. for specified periods of time. As the distilled water in the test tubes diffused across the membrane cup wall, the osmotic tablets expanded, and release of the blue dye/glycerol solution occurred in pulsatile manner. At preestablished intervals, the tubes were removed from the water bath, the capsules were removed from the tubes and placed in fresh tubes which were then placed back in the water bath. The used tubes in the meantime were analyzed for water volume, and aliquots were taken and analyzed for ultraviolet absorbance using a 1.000 cm cell, measuring at 408 nm. The delivery rate of blue dye/glycerol solution from the capsule was calculated from the recorded absorbance by converting the absorbance to the weight released (in milligrams) using a predetermined extinction coefficient, and dividing the weight thus determined by the duration of the interval between samples (in days).

Figure 2A:
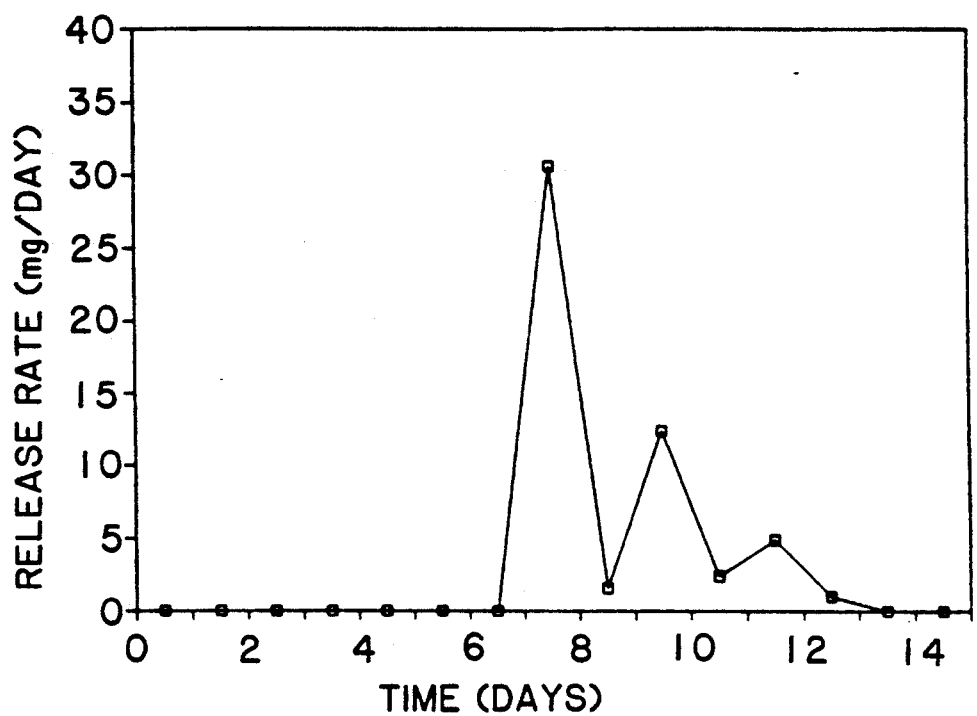
FIG. 2A is a plot of release rate vs. time for a test species in a pulsatile drug delivery device constructed and operated in accordance with the principles of this invention.
Figure 2B:
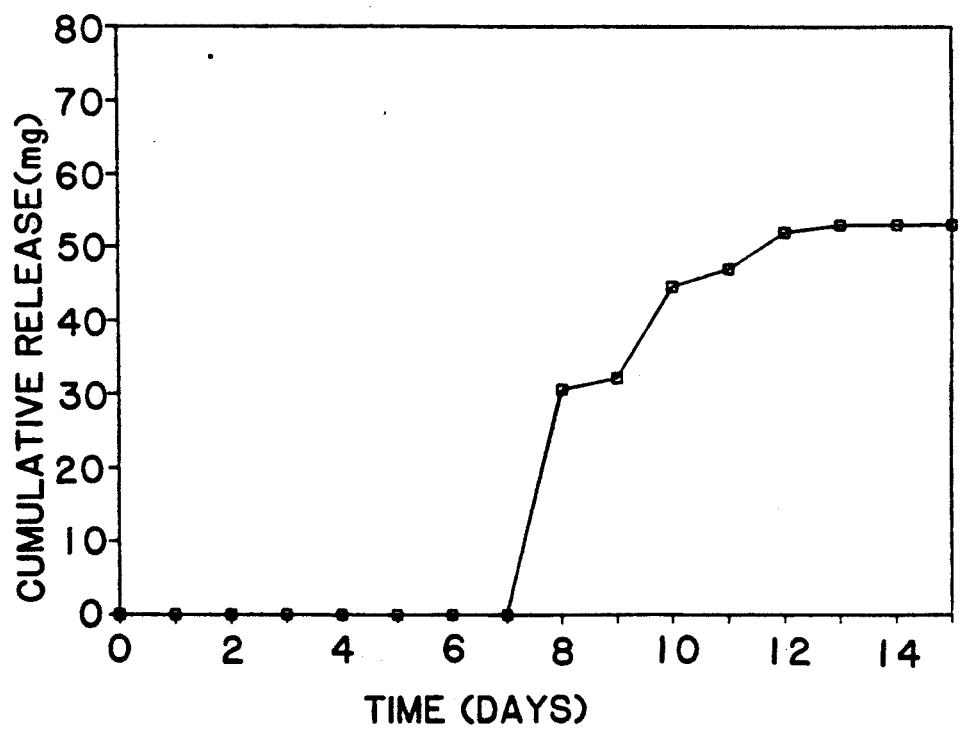
FIG. 2B represents the same experiment as FIG. 2A, and is a cumulative plot of the amount of test species released in the experiment.

The results are shown in FIG. 2A where the delivery rate is shown as a function of time, and in FIG. 2B where the cumulative delivery is shown. The pulsatile effect is evident from these Figures.

EXAMPLE 2

This example illustrates the effects of two variables on the pulsatile behavior of osmotic delivery devices constructed in accordance with this invention.

Devices identical in construction and composition to those used in Example 1 were used, except that the orifices were made with a 30-gauge needle (outer diameter 0.011–0.012 inch, 0.028–0.030 cm); the membrane cup was held inside a polycarbonate shell for enhanced support; and the piston was 0.200 inch (0.51 cm) in length. The variables were the location of the crimping wire along the length of the elastomeric drug bag covering the orifice end of the device (the location of the wire determines the stretchable length of the drug bag), and the length of the orifice. The crimping wire was varied between two positions, one providing the drug bag with a stretchable length of approximately 0.100 inch (0.25 cm), and the other a stretchable length of approximately 0.300 inch (0.76 cm). The length of the orifice channel was also varied between two values, one approximately 0.020 inch (0.051 cm) and the other approximately 0.025 inch (0.064 cm).

The devices were prepared according to the procedures of Example 1. A series of devices were also prepared as controls with no pulsatile effect. Pumps prepared for use as controls had a drug reservoir made entirely of polycarbonate and thus completely rigid. A pre-formed orifice was molded into the polycarbonate at the top of the reservoir, the orifice having a diameter of 0.020 inch (0.05 cm) and an average length of 0.100 inch (0.25 cm). The contents of the control pumps were the same as those of the test pumps.

Figure 3A:
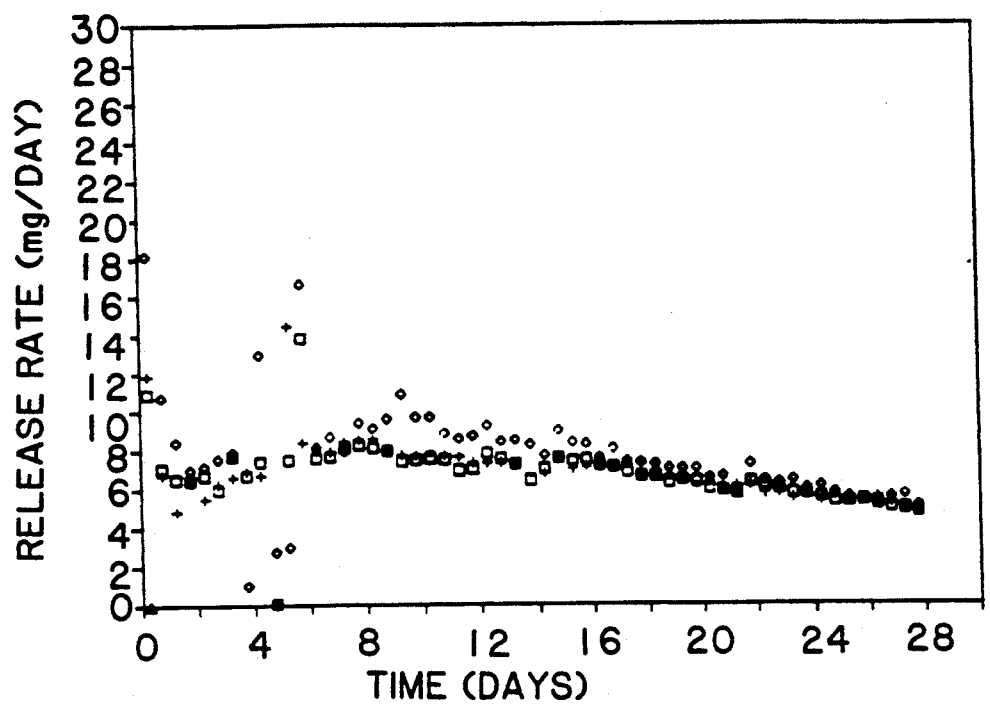
FIG. 3A represents a control experiment using a device which did not contain the pulsatile delivery features of the present invention. This and all subsequent figures are plots of release rate vs. time.

All devices were tested uniformly according to the procedures of Example 1, and the results of all experiments in terms of delivery rate as a function of time are shown in FIGS. 3A through 3F, as follows:

FIG. 3A: control experiment; no pulsatile effect. Three individual controls are shown, represented on the plot by squares, diamonds and crosses, respectively.

Figure 3B:
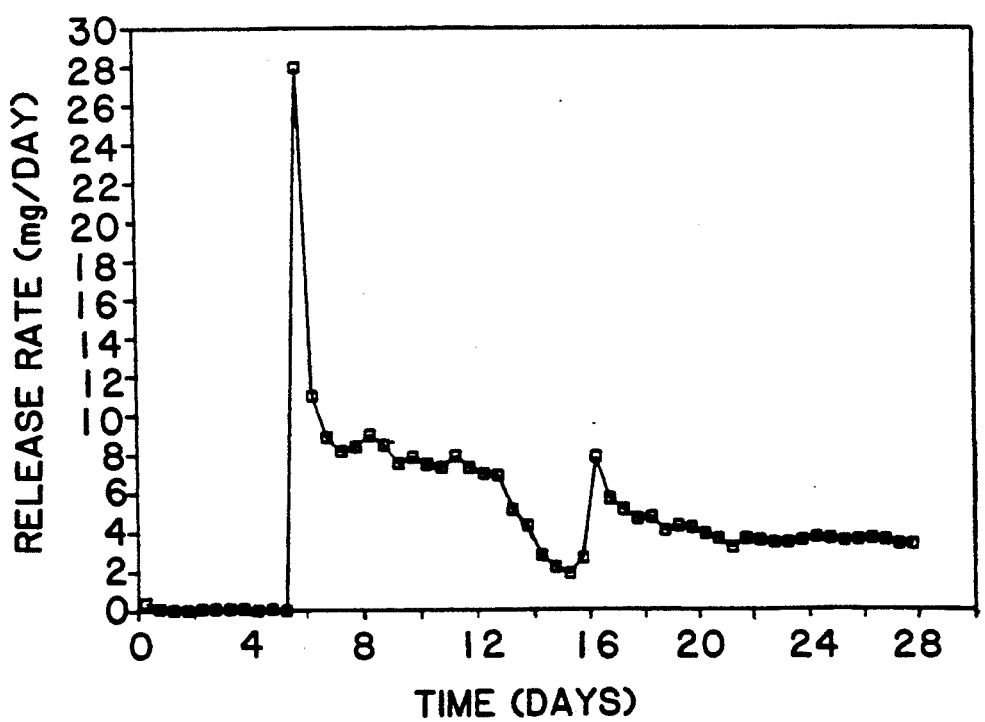
FIGS. 3B through 3F and 4A through 4E are plots of pulsatile delivery using devices containing the features of the present invention, the figures varying among themselves in terms of certain structural features of the device used to obtain the data.
Figure 3C:
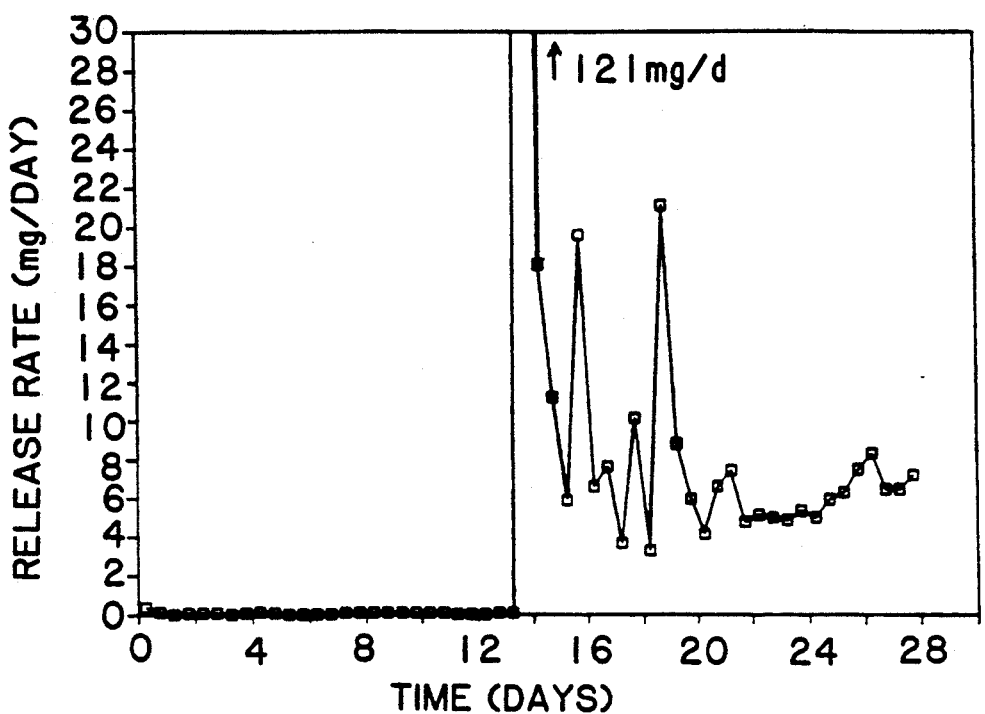
Figure 3D:
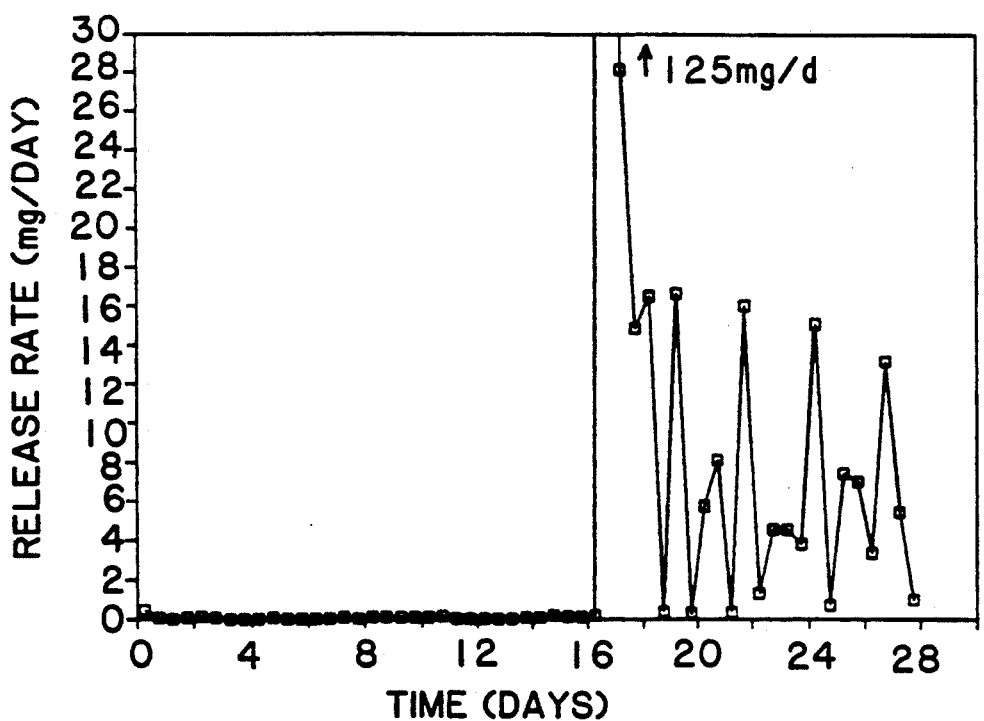
Figure 3E:
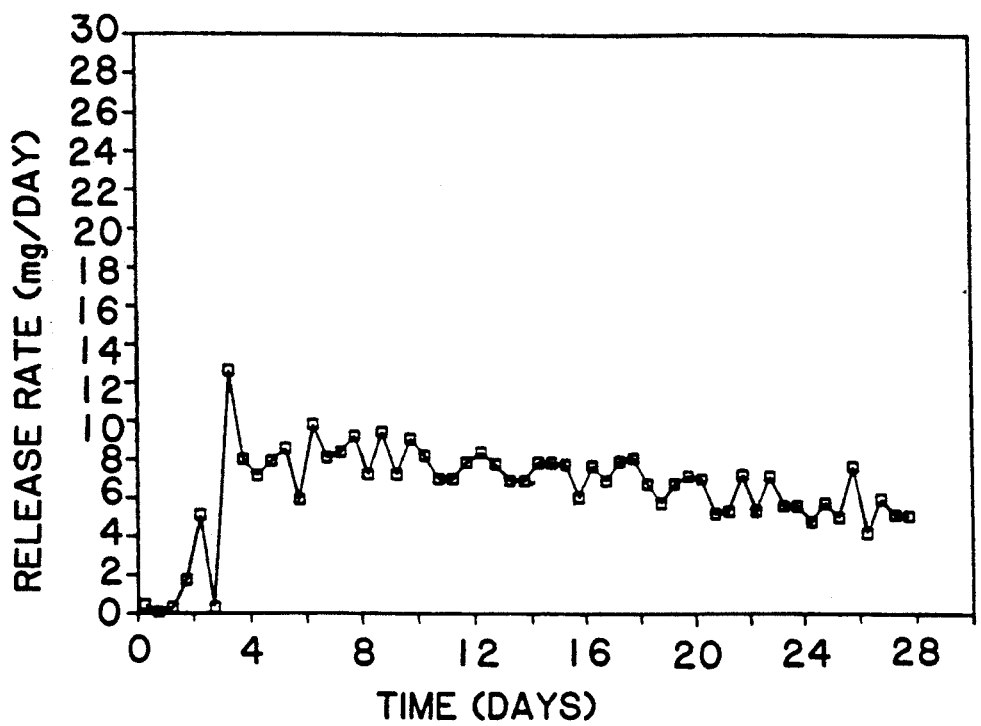
Figure 3F:
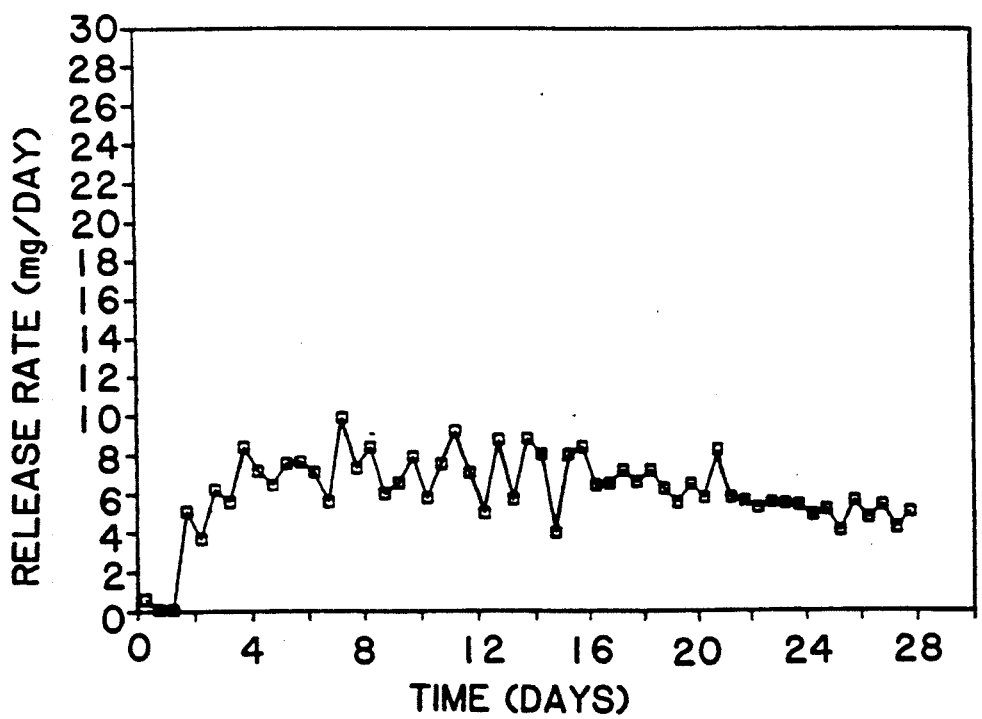

FIG. 3B: stretchable length of elastomeric bag: 0.300 inch; orifice channel length: 0.025 inch FIGS. 3C and 3D: stretchable length of elastomeric bag: 0.100 inch; orifice channel length: 0.025 inch FIGS. 3E and 3F: stretchable length of elastomeric bag: 0.300 inch; orifice channel length: 0.020 inch From these Figures, one may conclude that the pulsatile effect can be achieved over a range of the stretchable length of the elastomeric bag as well as over a range of the orifice channel length, and that the pulsatile effect appears to have a greater dependency on orifice length over the range tested.

EXAMPLE 3

This example is a further illustration of the effect of the orifice channel length on the pulsatile behavior.

Two orifice channel lengths were used—0.020 inch (0.051 cm) and 0.040 inch (0.102 cm). The devices were otherwise constructed as described in Example 2, with the crimping wire positioned to provide the drug bag with the longer stretchable length, and a 25-gauge needle used to form the orifices.

Figure 4A:
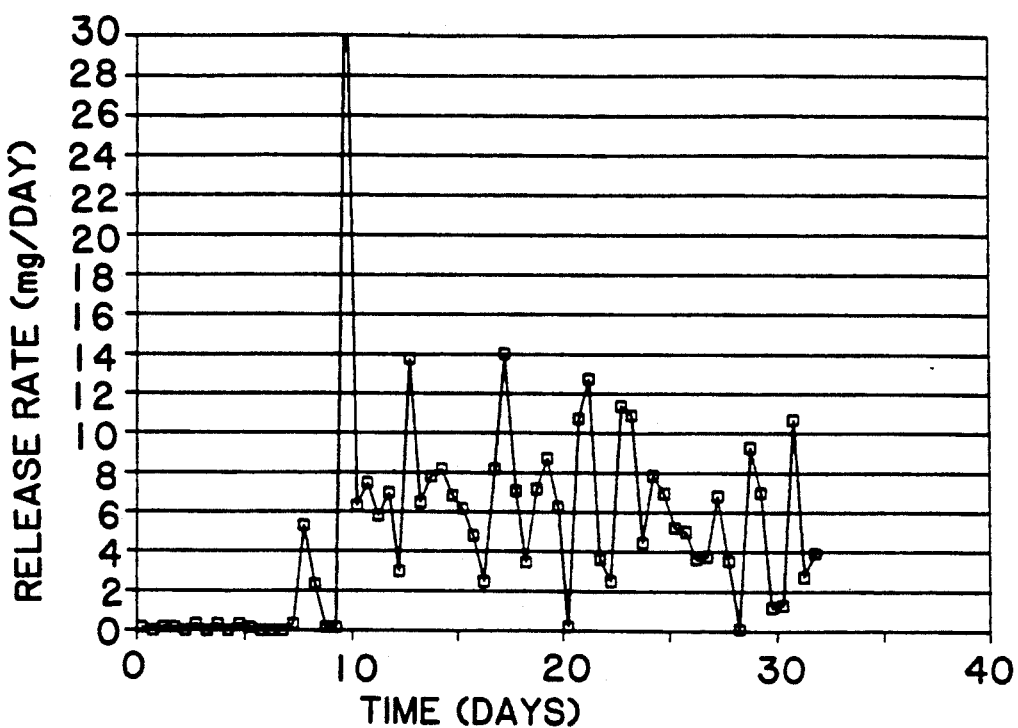
Figure 4B:
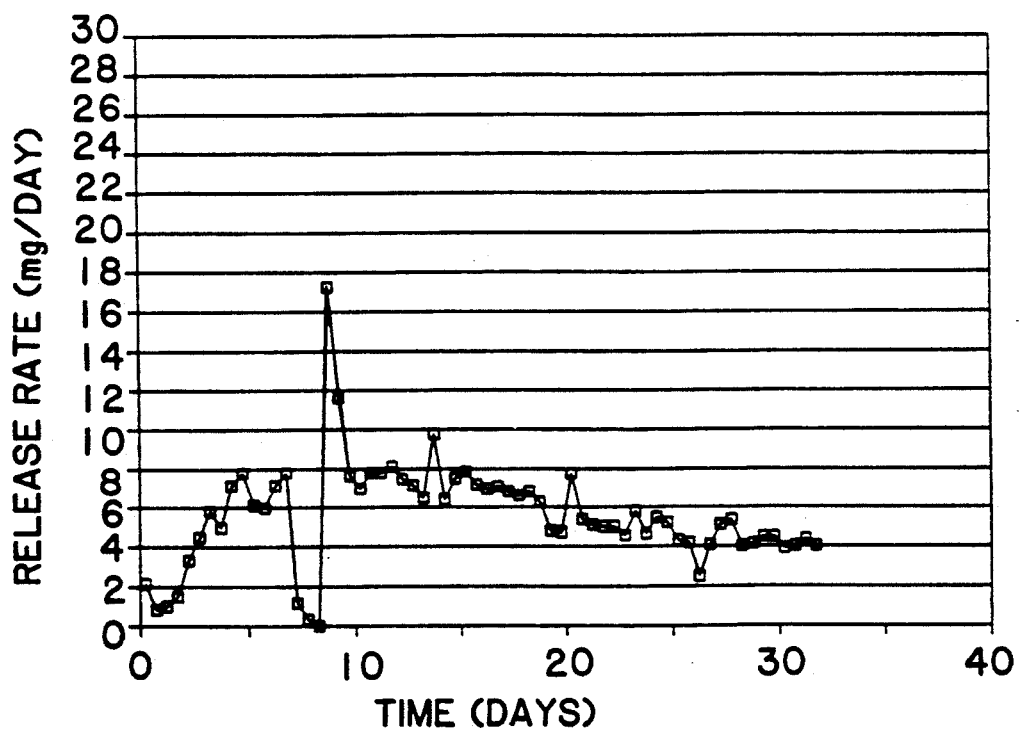

The devices were prepared and tested according to the procedures in the preceding examples, and the results in terms of delivery rate as a function of time are shown in FIGS. 4A through 4E, as follows:

FIGS. 4A and 4B: orifice channel length 0.020 inch

Figure 4C:
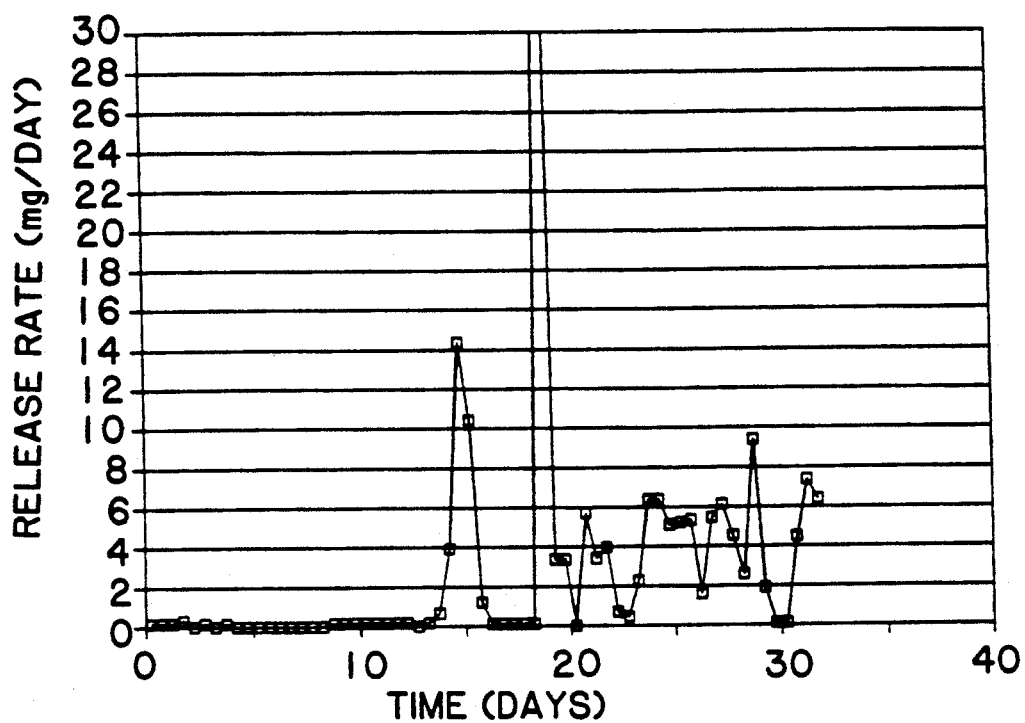
Figure 4D:
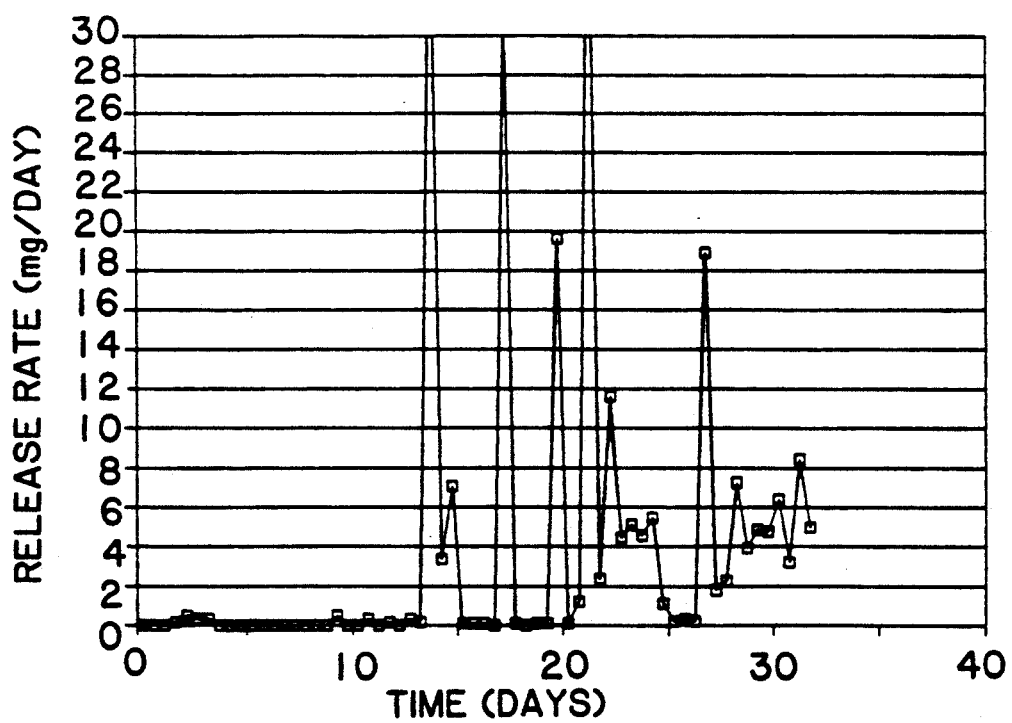
Figure 4E:
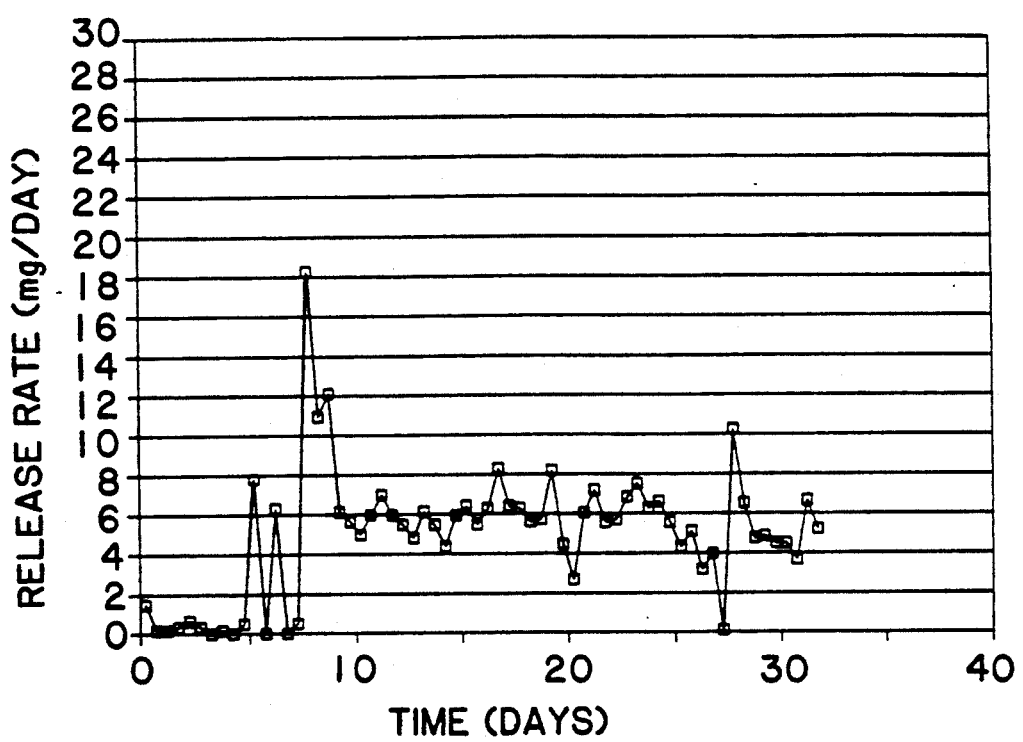

FIGS. 4C, 4D and 4E: orifice channel length 0.040 inch

While some of the variations seen in these figures are attributable to other system parameters which varied among these experiments, the results generally show that a longer orifice channel provides a more pulsatile delivery.

The foregoing is offered primarily for purposes of illustration. It will be readily apparent to those skilled in the art that the materials, dimensions, manufacturing procedures and other parameters of the system may be further modified or substituted in various ways without departing from the spirit and scope of the invention.

What is claimed is:

1. An osmotically driven device for placement in an aqueous environment for pulsatile delivery of a beneficial agent to said environment, said device comprising:

an enclosure defined by an enclosing wall, at least a portion of said enclosing wall being permeable to moisture, said enclosing wall containing an orifice surrounded by an elastomer material of at least about 0.03 cm in thickness, said elastomer material, when relaxed, closing said orifice to substantially prevent fluid passage therethrough and, when stretched by a pressure differential across said enclosing wall, opening said orifice to permit fluid passage, wherein said orifice is a puncture formed by piercing said elastomer material with a piercing member having an outer diameter of not more than about 0.015 cm.

2. An osmotically driven device in accordance with claim 1 in which said elastomer material is a styrene-butadiene copolymer.

3. An osmotically driven device in accordance with claim 1 in which said elastomer material is at least about 0.06 cm in thickness, and said orifice is a puncture formed by piercing said elastomer material with a piercing member having an outer diameter of not more than about 0.010 cm.

4. An osmotically driven device in accordance with claim 1 further comprising a moisture-absorbing material and a beneficial agent retained in said enclosure, said moisture-absorbing material adjacent to said portion of said enclosing wall which is permeable to moisture, and said beneficial agent adjacent to said orifice, and in which said elastomer material and said orifice are constructed such that continuous absorption of moisture from a physiological environment causes said orifice to open to release said beneficial agent intermittently.

5. An osmotically driven device in accordance with claim 4 in which said orifice opens to release said beneficial agent intermittently at intervals of from about six hours to about two days.

6. An osmotically driven device in accordance with claim 1 in which said enclosure is an elongate enclosure having a longitudinal axis and containing a partition capable of moving along said longitudinal axis, said orifice located on one side of a location along the longitudinal axis of said enclosure defined as an initial position of said partition, and said portion of said enclosing wall which is permeable to moisture located on the other side of said initial position.

7. An osmotically driven device in accordance with claim 6 further comprising a moisture-absorbing material and a beneficial agent retained in said enclosure, said moisture-absorbing material on one side of said partition adjacent to said portion of said enclosing wall which is permeable to moisture, and said beneficial agent on the other side of said partition adjacent to said orifice.

8. An osmotically driven device in accordance with claim 6 in which said partition is substantially non-deformable and is capable of moving longitudinally in said enclosure with substantially no resistance from any interior wall of said enclosure.

9. An osmotically driven device in accordance with claim 7 in which said partition is substantially non-deformable and is capable of moving longitudinally in said enclosure with substantially no resistance from any interior wall of said enclosure.

* * * * *